(12) United States Patent
Keles

(10) Patent No.: US 6,976,838 B1
(45) Date of Patent: Dec. 20, 2005

(54) NEWLY DEVELOPED FACE BOW AND PROTRACTION HEADGEAR IN CORRECTION OF ANTERIOR OPENBITE CLASS III PATIENTS

(76) Inventor: Ahmet Ozlem Keles, Halaskargazi Cad Halas Apt. No. 275/4, Osmanbey, Istanbul (TR) 80220

( * ) Notice: Subject to any disclaimer, the term of this patent is extended or adjusted under 35 U.S.C. 154(b) by 0 days.

(21) Appl. No.: 10/148,631
(22) PCT Filed: Nov. 30, 1999
(86) PCT No.: PCT/TR99/00051

§ 371 (c)(1),
(2), (4) Date: Oct. 15, 2002

(87) PCT Pub. No.: WO01/39686

PCT Pub. Date: Jun. 7, 2001

(51) Int. Cl.[7] .................................................. A61C 7/00
(52) U.S. Cl. ........................................................ 433/5
(58) Field of Search ...................... 433/5, 7, 18; 602/17

(56) References Cited

U.S. PATENT DOCUMENTS

| 2,151,458 A | * | 3/1939 | Allen | ........................... | 602/17 |
| 4,988,291 A | * | 1/1991 | Grummons | ..................... | 433/5 |
| 5,158,451 A |   | 10/1992 | Pourcho |  |  |
| 5,810,583 A | * | 9/1998 | Doyle | ........................... | 433/5 |

* cited by examiner

Primary Examiner—Melba Bumgarner
(74) Attorney, Agent, or Firm—Hodgson Russ LLP

(57) ABSTRACT

A face bow and protraction headgear to correct the anterior open bite in dentally Class III open bite cases. The appliance consists of a face bow and forehead pad. The face bow has intraoral and extraoral components custom made individually for each patient. The intraoral bow is inserted from the distal openings of tubes soldered to the extraoral face bow. The extraoral face bow extends backward to the front of the ear then turns upward and ends at the level of the hooks on the forehead pad. Only the forehead is used as anchorage unit. On both sides of the pad, adjustable wire hooks are placed which allow maintaining the distance from the forehead pad hooks to the face bow hooks. Heavy elastics are attached in between the hooks of the face bow and the hooks on the forehead pad.

8 Claims, 1 Drawing Sheet

NEWLY DEVELOPED FACE BOW AND PROTRACTION HEADGEAR IN CORRECTION OF ANTERIOR OPENBITE CLASS III PATIENTS

BACKGROUND OF THE INVENTION

Treatment of a malocclusion characterized by open bite with Class III pattern can be difficult to treat since such a malocclusion develops as a result of the interplay of many different etiological factors. Skeletal open bite cases are usually characterized by an increase in the vertical growth of the maxillary posterior dentoalveolar segments. The application of conventional reverse headgears and application of the mesially directed force below the center of resistance of maxillary dentition would tend to increase the anterior open bite. An intrusion of posterior teeth becomes more difficult with older age, mechanical treatment options are limited in adult patients. Orthognathic surgery is indicated in adult patients with severe open bite and Class III skeletal pattern with retrognthic maxilla. For the treatment of borderline cases, and those individuals who are reluctant to surgery, the search for a new treatment modalities continues.

Previous studies have shown both the effects and side effects of the application of protraction forces on the maxillary complex. Until today most of the appliances which were developed could not prevent the upward and forward rotation of the maxilla. The most important things to be considered in maxillary protraction are the point of the force application and the direction of the force. As the mandible is attached to the head with temporomandibular joint, it rotates around the condylar axis when opening and closing the mouth. It is impossible to stabilize the force system in reverse pull headgear, which takes anchorage from the chin, since the movement of the mandible doesn't allow us to apply a consistent force. Another very important aspect, which needs to be considered, is the uncertain effect of orthopedic forces on the TMJ and on mandibular growth. In growing children force application'to the chin by reverse-pull headgear causes downward and backward rotation of mandible.

SUMMARY OF THE INVENTION

To eliminate the above listed adverse effects of the previously used reverse-pull headgears, I have developed a face bow and a protraction headgear design. My aim in planning this headgear design was to rotate the maxilla with downward and backward direction in Class III patients with anterior openbite. In my appliance design, the point of force application is positioned above the center of resistance of maxilla. I have not used the mandible for anchorage because of the unknown effects of distal force on the TMJ. Full coverage acrylic cap splint type-RME appliance was used intraorally to release the maxilla prior to the protraction.

DETAILED DESCRIPTION

Figure 1:
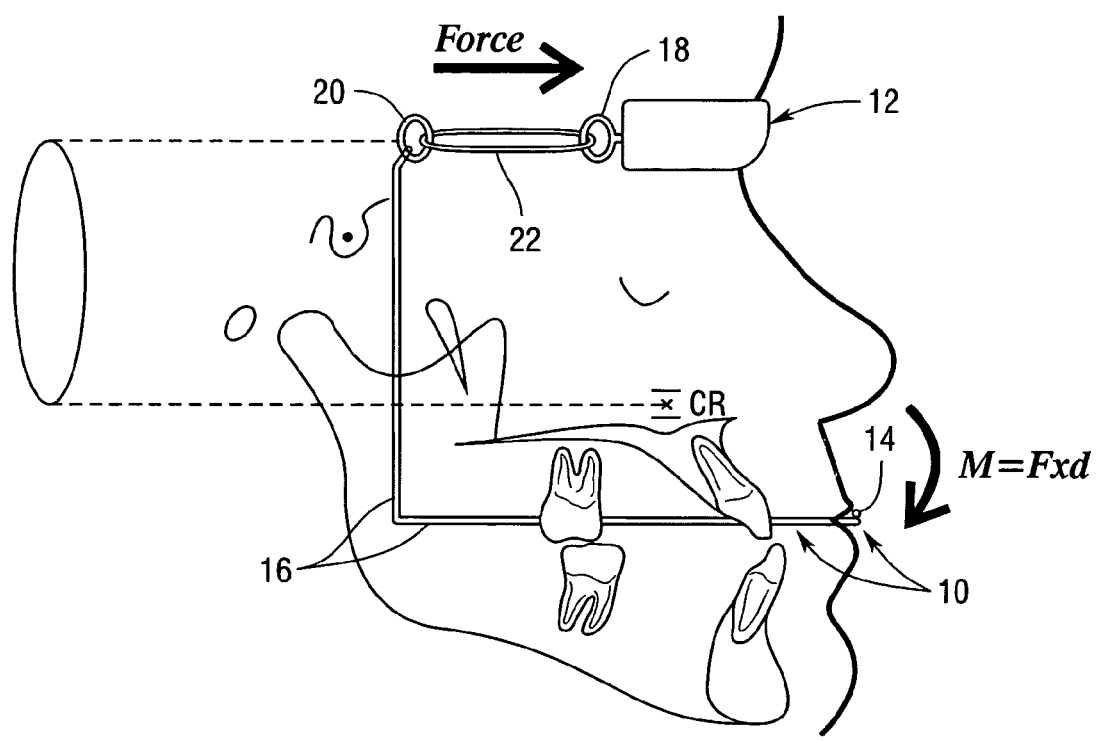
FIG. 1 is a diagrammatic view illustrating the orthodontic appliance and method of the present invention.

The appliance of the invention comprises a face bow 10 and forehead pad 12. The face bow has intraoral 14 and extraoral 16 components and is custom made individually for each patient. The intraoral bow 14 (1.55 mm in diameter) is inserted from the distal openings of the tubes. It includes at least one component 15 for connecting the bow 14 to the patient's teeth, for example an acrylic splint, as is well known to those skilled in the art. It is soldered to the extraoral face bow 16, 10 mm in front of the incisor region of the cap splint. The extraoral face bow 16 (3 mm in diameter) extends backward until the front of the ear then turns upward and ends at the level of the hooks 18 on the forehead pad 12. The distance between the wire hooks on the forehead pad and the hooks 20 of the extraoral face bow can be adjusted as 3 cm. In this extraoral appliance design only the forehead was used as anchorage unit. On both sides of the pad, adjustable wire hooks (1.2 mm in diameter) were placed which allowed us to maintain the distance from the forehead pad hooks to the face bow hooks. For patient comfort and for better adaptation to the forehead, the inner surface of the pad was covered with silicone and soft-liner material. Heavy elastics 22 (2H(3/16") 14 Oz. Ormco Cooperation) were attached in between the hooks of the face bow and the hooks on the forehead pad. 750 g of protrusive force was applied and the force was oriented parallel to the Frankfort horizontal plane. The Extraoral appliance was worn for at least 17 hours per day for 6 months. The force-moment systems of the extraoral appliance are demonstrated in FIG. 1.

Biomechanics for force moment system of newly developed face bow design and reverse headgear:
d: Distance
F: Force
M: Moment
CR: Center of resistance This newly developed face bow and protraction headgear design is accepted for publication from American Journal of Orthodontics and Dentofacial Orthopedics as original article. It will be published in January 2000 issue with the title of "The effects of modified headgear on maxilla".

In this newly developed appliance design, the force was applied at the forehead pad level, which is above the center of resistance of maxilla. The direction of the force was forward and parallel to the Frankfort horizontal plane. In Class III anterior open bite and high angle cases the application of conventional reverse headgears were not indicated because of forward and upward rotation of maxilla and downward and backward rotation of mandible.

In this newly developed appliance design, support was taken only from the forehead. One of the advantages of this newly developed headgear was that it had no effect on the mandible. The influence of distal forces on TMJ is not clear.

The other advantage of not using chin as support for protraction was the difficulty in applying a consistent force because of the movements of the lower jaw.

From the point of patient comfort, this newly developed appliance was accepted easily because of the freedom of the mandible and aesthetic appearance.

If we look at the skeletal changes related to maxilla, the maxilla are rotated in a downward and backward direction. The SN palatal plane angle is increased. The ANS is moved in a downward direction. Maxilla are advanced anteriorly. Functional occlusal plane is rotated in a downward and backward direction.

If we look at the dental changes, Class III molar relationship was corrected, anterior open bite was eliminated, overjet was improved. Maxillary incisors were retroclined, i.e. a decrease in SN to maxillary incisor angle, and extruded. This newly developed modified headgear design can be used very effectively in anterior open bite patients with Class III dental malocclusion.

The patients who have deficient premaxilla excessive posterior maxillary growth and patients who do not show incisors during smiling can be treated effectively with this newly developed device.

What is claimed is:

1. An orthodontic appliance comprising:
   a) a face bow comprising an intraoral portion for connection to a patient's teeth and an extraoral portion extending from the intraoral portion to locations forwardly of both of the patient's ears;
   b) a forehead pad serving as the sole means of extraoral support for the appliance; and
   c) elastic means connected to opposite ends of the forehead pad and to the locations on the extraoral face bow portion for applying force above the center of resistance of maxilla to rotate the maxilla with downward and backward direction in Class III patients with open bite.

2. The orthodontic appliance according to claim 1 wherein the intraoral face bow portion extends generally horizontally outwardly in a direction away from where the patient's teeth and wherein the extraoral face bow portion has a first section extending generally horizontally and rearwardly from the intraoral face bow portion and a pair of second sections extending generally vertically and forwardly of the patient's ears and terminating at locations at the general level of the patient's forehead.

3. The orthodontic appliance according to claim 2, wherein the elastic means is connected to the pair of second sections of the extraoral face bow portion at a location at the general level of the patient's forehead.

4. The orthodontic appliance according to claim 1, further including at least one component for connecting the intraoral face bow portion to the patient's teeth.

5. The orthodontic appliance according to claim 4, wherein the component is an acrylic splint.

6. An orthodontic appliance comprising:
   a) a face bow comprising an intraoral portion for connected to components for securing to a patient's teeth and extending from the patient's mouth where the intraoral portion joins an extraoral face bow portion having a pair of spaced-apart sections each extending along opposite sides of the patient's face to ends located forwardly of the patient's ears and at the general level of the patient's forehead;
   b) a forehead pad having opposite ends and serving as the sole means for providing extraoral anchorage for the appliance; and
   c) a pair of elastic members each connected to a corresponding one of the ends of the extraoral face bow sections and the ends of the forehead pad for applying force above the center of resistance of maxilla to rotate the maxilla with downward and backward direction in Class III patients with open bite.

7. The orthodontic appliance according to claim 6, wherein each of the sections of the extraoral face bow portion has a first part extending generally horizontally and rearwardly relative to the patient's teeth and a second part extending generally vertically from the first part to the end at the general level of the patient's forehead.

8. The orthodontic appliance according to claim 6, wherein components for securing to the patient's teeth comprise acrylic splints.

\* \* \* \* \*